United States Patent [19]
Vivenzio et al.

[11] Patent Number: 5,435,296
[45] Date of Patent: Jul. 25, 1995

[54] ENDOSCOPE HAVING CRIMPED AND SOLDERED CABLE TERMINATOR

[75] Inventors: Robert L. Vivenzio, Auburn; Allan I. Krauter, Syracuse; Michael P. Kehoskie, Jordan, all of N.Y.

[73] Assignee: Welch Allyn, Inc., Skaneateles Falls, N.Y.

[21] Appl. No.: 75,330

[22] Filed: Jun. 11, 1993

[51] Int. Cl.⁶ .................................................. A61B 1/01
[52] U.S. Cl. .................................... 600/146; 604/95; 140/76
[58] Field of Search ................ 140/76; 29/515; 228/132–135; 165/47; 74/502.3–502.6; 403/265, 274, 275; 128/4, 6; 604/95; 174/84 C

[56] References Cited

U.S. PATENT DOCUMENTS

| | | | |
|---|---|---|---|
| 3,203,078 | 8/1965 | Utsin | 174/84 C X |
| 3,333,047 | 7/1967 | Geoffroi | 174/84 C X |
| 4,035,577 | 7/1977 | Loeber | 140/76 X |
| 4,135,296 | 1/1979 | Kami et al. | 174/84 C X |
| 4,735,259 | 4/1988 | Vincent | 165/47 |
| 4,770,185 | 9/1988 | Silverstein et al. | 128/4 X |
| 4,796,607 | 1/1989 | Allred, III et al. | 128/4 |

*Primary Examiner*—Richard J. Apley
*Assistant Examiner*—John Mulcahy
*Attorney, Agent, or Firm*—Harris Beach & Wilcox

[57] ABSTRACT

An Endoscope having at least one control cable wherein a helically wound cylindrical spring is passed over one end of the cable and is crimped into deforming contact against the cable. Melted solder is flowed over and through the spring to wet the spring and the cable surfaces. The solder is allowed to solidify thus creating a strong joint between the cable and the spring.

9 Claims, 4 Drawing Sheets

ENDOSCOPE HAVING CRIMPED AND SOLDERED CABLE TERMINATOR

BACKGROUND OF THE INVENTION

This invention relates to a method and apparatus for terminating one end of a cable and, in particular, to a high strength device for terminating the distal end of a cable used for articulating the viewing head of an endoscopic or borescopic insertion tube.

Most endoscopes and borescopes are provided with an insertion tube having a bendable steering section which allows the viewing head mounted at the distal end of the tube to be guided along what sometimes might be a tortuous path of travel. Typically, the bendable steering section is mounted immediately behind the viewing head of the instrument and is articulated by means of a plurality of control cables. A steering section of this nature is disclosed in U.S. Pat. No. 4,796,607.

The proximal ends of the cables are connected by pulleys or gear racks to control knobs on the handle of the insertion tube and are passed through the steering section and an end plate located at the distal end of the steering section. The end plate is secured to the viewing head of the instrument. The distal end of each cable is terminated by slipping brass or stainless steel cylinders thereover and the cylinder is soldered to the cable. During articulation the terminated end of the cables are pulled with some force against the end plate.

The brass or stainless steel cylinder termination devices have certain advantages that make them attractive for use in endoscopic applications. They are well suited for terminating small diameter cables and the joint between the cable and the termination cylinder is easily formed. The solder used in the joint penetrates the wire strands of the cable to strengthen the joint and to prevent the wire strands from unwrapping in the event the termination device fails. Unraveled strands can harm adjacent parts of the instrument or find their way into the target region that is undergoing inspection.

SUMMARY OF THE INVENTION

It is therefore an object of this invention to improve devices for terminating wire cables and, in particular, for terminating small diameter cables of the type generally used in endoscopic or borescopic steering sections.

It is a further object of the present invention to increase the initial strength of a device used to terminate a wire cable.

It is a still further object of the present invention to increase the useful life of a cable terminating device that is subjected to repeated or sustained loads.

It is another object of the present invention to provide a cable terminating unit that has all the advantages of the current designs and in addition, is easy to assemble and has increased joint strength.

Still another object of the present invention is to join a terminating sleeve to a cable using a combined mechanical and solder joint.

These and other objects of the present invention are attained by means of a cable terminating device that includes a helically wound cylindric spring that is slidably mounted upon the distal end of a cable. The spring is crimped or deformed inwardly to preferably lock against the cable. Melted solder is flowed over and through the spring to wet both the cable and the spring. The solder penetrates between the spring coils and impregnates the cable strands to form a greatly enhanced solder joint upon solidification of the solder.

BRIEF DESCRIPTION OF THE DRAWINGS

For these and other objects of the present invention, reference is had to the following detailed description of the invention that is to be read in association with the following drawings, wherein.

DETAILED DESCRIPTION OF A PREFERRED EMBODIMENT

Figure 1:
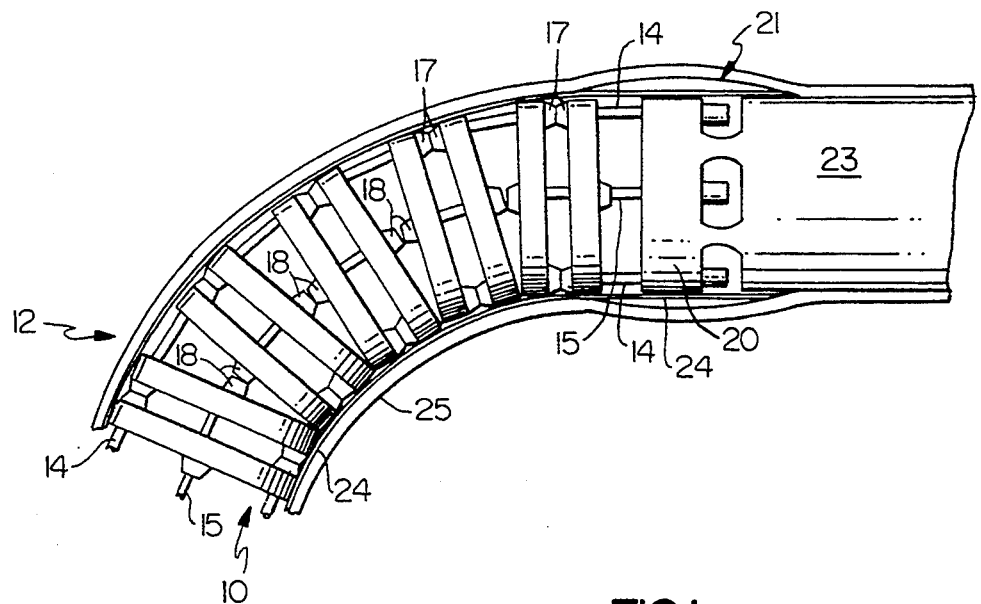
FIG. 1 is a partial side elevation showing the bending section and the viewing head of an endoscopic or borescopic insertion tube which utilizes termination devices embodying the teachings of the present invention.

Referring initially to FIG. 1, there is shown the distal end of an endoscopic or borescopic insertion tube 10 which includes a steering section 12. The steering section contains a series of stacked circular washers that are slidably mounted on cables 14 and 15 made of twisted strands of stainless steel. Each washer contains two sets of spacer beads mounted on the opposing end faces thereof. The beads are placed at 90° intervals adjacent to the outer periphery of the washer with the beads in each set lying along a common diametrical line. The washers are covered by a metal or plastic braid 24 and thereover by a flexible elastomeric sheath 25.

As explained in greater detail in the previously noted U.S. Pat. No. 4,796,607, cable 14 is passed through beads 17—17 that are located on one face of each washer, while cable 15 is similarly passed through beads 18—18, located on the opposite face of each washer. In assembly, the beads are placed on the cables in an arrangement as shown in FIG. 1 with beads 17 on one washer riding in contact with the beads 17 on an adjacent washer. Similarly, beads 18 on one washer are mounted in riding contact with beads 18 on an adjacent washer. The cables are connected to individual control pulleys or gear racks located in the control handle of the instrument (not shown) with the distal end of the cables being passed through an end plate 20. A terminating device embodying the present invention is secured to the distal end of each cable that prevents the cable from being pulled back through the end plate.

The end plate 20 is connected by any suitable means to the viewing head 23 of the insertion tube. In the case of a video endoscope, the viewing head will contain a CCD imager for recording image data relating to a remote target within the viewing range of the instrument. The recorded image data is converted into electrical signals that are transmitted back through the insertion tube to the video section (not shown) for processing and viewing. The viewing head of the instrument can be articulated by pulling on selected cables. This, in turn, causes the associated terminating units to be pulled with some force against the end plate.

Figure 2:
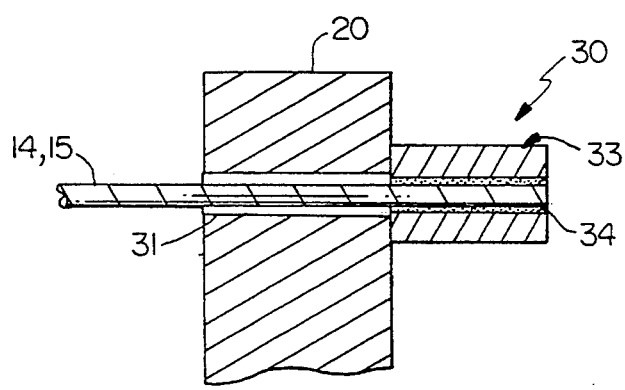
FIG. 2 is an enlarged side elevation in section, showing a prior art cable terminating device.

Turning now to FIG. 2, there is shown a typical terminating device 30 found in the prior art. The distal end of a steering cable 14, 15 is passed through an opening 31 formed in the end plate 20. A brass cylinder 33 is positioned over the distal end of the cable and a solder joint 34 is formed between the cylinder and the cable. Typically, the cable is about 0.02 inches in diameter and the terminator cylinder is about 0.10 inches long and has an outside diameter of about 0.043 inches and an inside diameter of about 0.028 inches. The solder joint, if properly formed, generally exhibits good strength at the time a load is initially applied to the cylinder. However, the joint can fail under repeated or sustained loading with failure being similar to load dependent creep failure. As noted above, one of the objects of the present invention is to increase the joint strength of a terminating unit without sacrificing the many advantages associated with this type of device.

Figure 3:
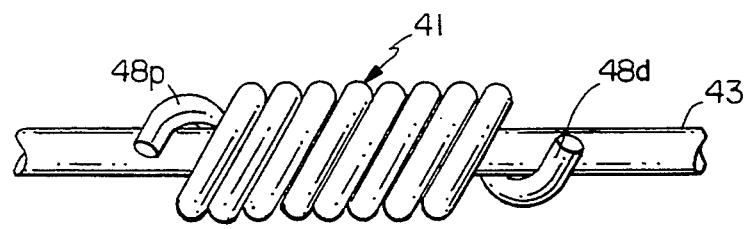
FIG. 3 is an enlarged side elevation showing a cylindrical spring mounted upon the distal end of a steering cable.
Figure 4:
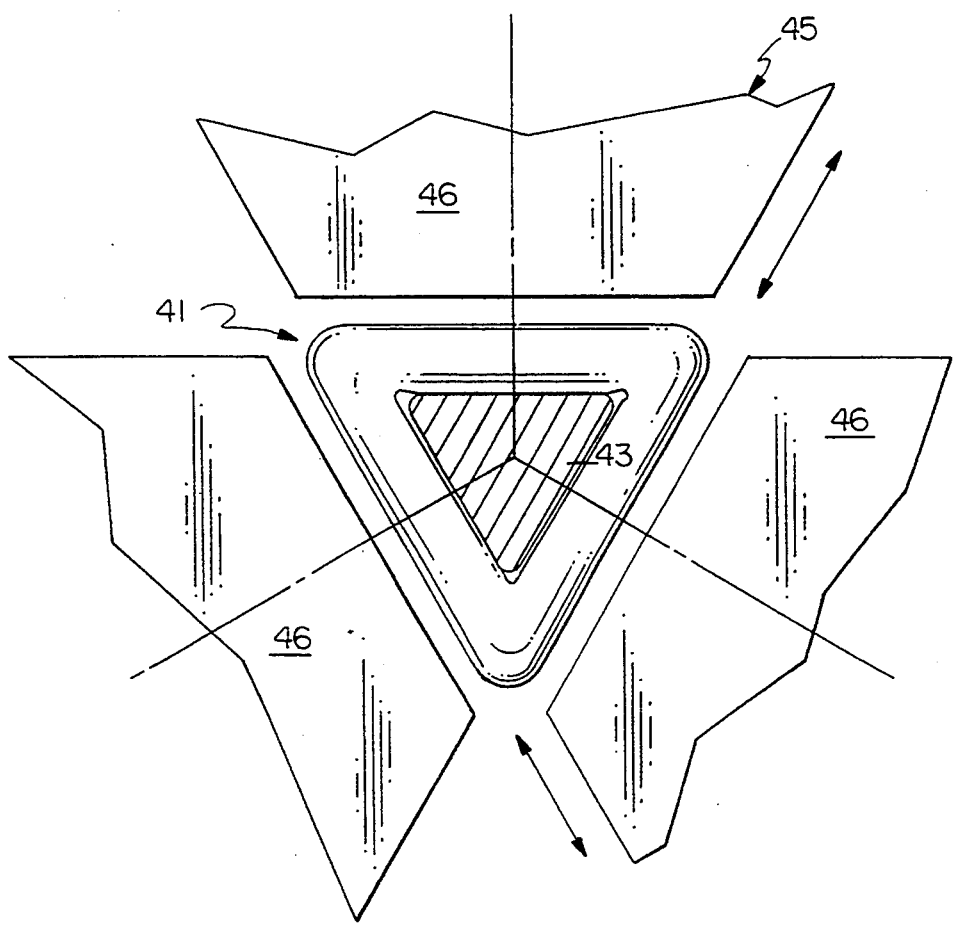
FIG. 4 is a greatly enlarged front view showing a spring being crimped into contact with a wire cable.

As illustrated in FIGS. 3–4, the terminating unit 40, (FIG. 5), of the present invention includes a cylindrical, helically wound spring element 41 formed of a single strand of stainless steel. The spring is initially slipped over the distal end of a cable 43 as shown in FIG. 3. When properly positioned on the cable, the spring is crimped or deformed inwardly along its entire length using a three jaw universal chuck 45 as illustrated in FIG. 4. The three jaws 46—46 of the chuck are equally spaced at 120° intervals and are driven into contact simultaneously with the spring to deform the spring into a triangular shape as shown. Preferably, the spring is crimped into locking contact against the cable to form a mechanical joint therebetween.

After crimping, melted solder 43 (FIG. 5) is flowed onto and through the spring to wet the spring surfaces and the cable. The solder penetrates the spring in the spaces between the coils which, during the crimping operation, are slightly opened and impregnates the wire strands of the cable. Upon solidification, the solder forms an extremely strong joint between the spring and the cable which is substantially free of cold joints. The solder also holds the strands of the cable together in the event that the cable does pull out of the spring under excessive loading. Keeping the strands together prevents damage to the endoscope or borescope that could be caused by ends of frayed cable strands.

Figure 5:
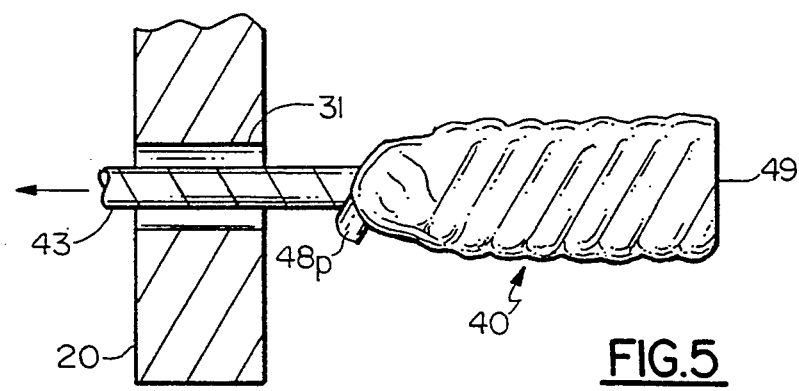
FIG. 5 is an enlarged side elevation showing one embodiment of the invention.

Excess cable distal of the joint as well as the distal end tang 48d (FIG. 3) is removed from the distal end of the unit to provide a substantially flat end face 49 (FIG. 5).

Extremely good termination for a 0.02 inch diameter stainless steel cable was obtained using an axially preloaded stainless steel spring having 0.03 inch inside diameter and a wire size of 0.012 inches. The spring had an axial length of about 0.100 inch and was crimped into the cable using a three jaw chuck. A crimping force of 500 to 1,000 pounds was applied by each jaw to the spring which caused the spring to deform the cable slightly showing that a mechanical joint was formed therebetween. A solder containing 96% tin and about 4% silver and having a melting temperature of about 430° F. was flowed over and through the spring to completely blanket the spring and fill the voids between the spring and the cable. The solder was allowed to cool, and the cable and distal tang were removed, thus completing the joint.

Cables terminated in the manner described above were load tested and shown to withstand a steady load of forty pounds for over a seven day period. This represents a marked improvement over terminating devices presently utilized in the prior art which fail under the same load conditions in considerably less time.

As exhibited in FIG. 5, the proximal end of the spring equipped terminating unit 40 still retains the proximal end tang 48p which faces the end plate 20. The tang typically protrudes outside the solder envelope 43 and thus has a potential to cause damage to components of the endoscope or borescope. Additionally, the tang accepts some of the axial loading on the cable and may shift its position upon application of an initial load thereby affecting cable performance during a steering maneuver.

Figure 6:
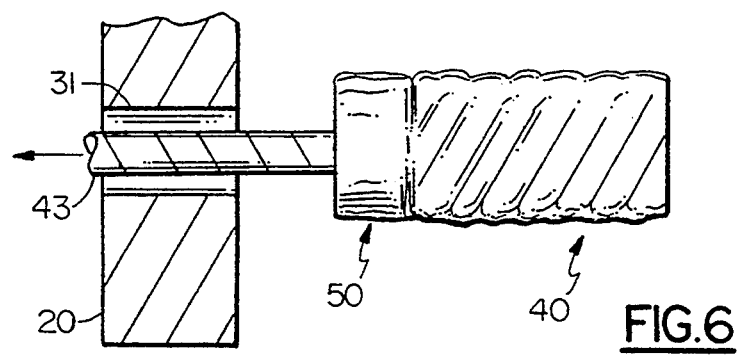
FIG. 6 is an enlarged side elevation showing another embodiment of the invention.

To avoid problems associated with untrimmed proximal tangs, a stainless steel washer 50 (FIG. 6) may be placed over the cable at the proximal end of the spring. During assembly, the spring is initially crimped to the cable as explained above. The jaws of the crimping tool are brought into contact with the washer and sufficient force is applied to hold the washer firmly in the jaws. The cable is pulled through the washer with sufficient axial force to bend the proximal end tang of the spring back into the crimped spring structure. The jaws of the tool are then tightened to crimp both the washer and the spring simultaneously into deforming locking contact with the cable. Finally, the structure is soldered as noted above and the distal ends of the cable and the spring are trimmed to form a flat distal end face on the assembly.

Figure 7:
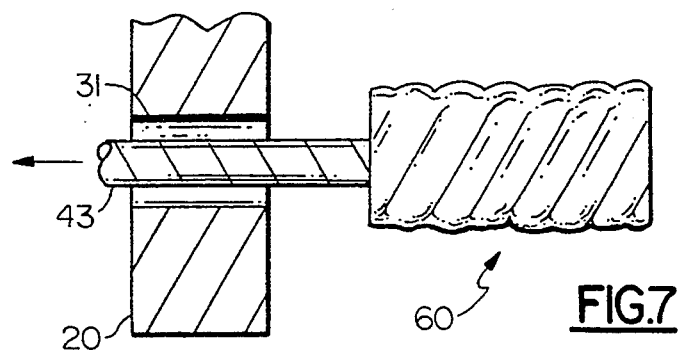
FIG. 7 is an enlarged side elevation showing a still further embodiment of the invention.

A terminating structure 60 as illustrated in FIG. 7 can also be obtained by first crimping the spring upon a rigid solid steel mandrel having a diameter slightly greater than the diameter of the cable. After the initial crimping operation is completed, one end of the pre-crimped spring is trimmed to remove the end tang. The spring is removed from the mandrel and mounted upon the distal end of the cable with the trimmed end toward the proximal end of the cable. The spring is now further crimped into deforming contact against the cable, and the solder joint is formed. The distal end of the spring and the cable are trimmed as previously noted to produce the structure illustrated in FIG. 7. Ten terminator units of the type shown in FIG. 7 were tested for initial strength. The average load at failure was 61 pounds with the minimum load at failure being 53 pounds. The time to failure in all cases exceeded one week. It was also found that about a 12% increase in initial load strength can be obtained by covering the distal end of the spring and the cable with solder after the distal end trimming operation has been completed.

Figure 8:
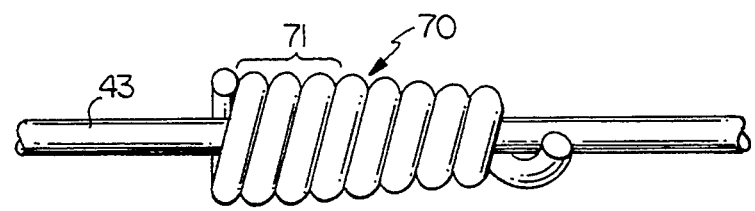
FIGS. 8-10 illustrate the steps in producing a still further embodiment of the invention.
Figure 9:
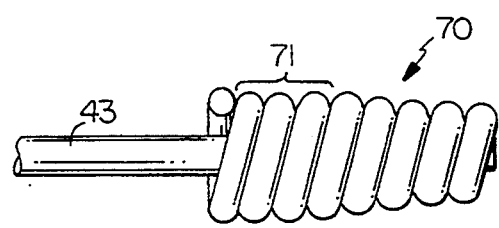
Figure 10:
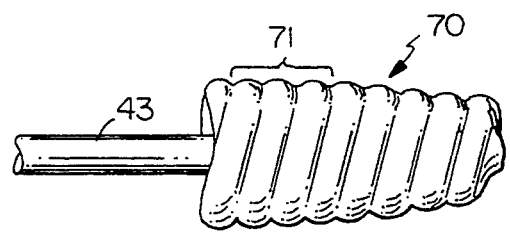

A still further embodiment of the present invention is illustrated by FIGS. 8–10. In this embodiment of the invention a spring 70 having an inside diameter of 0.025 inches and wire size of 0.009 inches is placed on the distal end of a 0.02 inch diameter cable 43. The distal end of the spring is then crimped into contact against the cable using a three jaw chuck. In this case the jaws of the chuck are tapered so that the spring is tapered downwardly as shown in FIG. 8 from the proximal end thereof towards the distal end so that each successive coil in the crimped section exerts a higher holding force on the cable. From one to three coils 71 at the proximal end of the spring remain uncrimped and as a result no tang is formed at the proximal end of the spring.

After crimping, the distal end of the cable and distal end tang on the spring are removed as shown in FIG. 9. Solder is then flowed over and through the spring and permitted to wet the spring and the cable to complete the joint therebetween as shown in FIG. 10.

Terminated cables using the tapered spring arrangement have been constructed and tested. The termination units exhibited an average breaking strength at initial loading about that of a bare cable, that is, a breaking strength of about 70 pounds. Long term steady load testing also confirms that this type of termination unit lasts far longer than terminating devices presently found in the prior art.

Although the unit illustrated in FIG. 10 includes a solder joint, it is believed that the use of solder in this embodiment is not necessary because of high strength exhibited by the mechanical joint produced by the crimping operation.

While this invention has been explained with reference to the structure disclosed herein, it is not confined to the details set forth and this application is intended to cover any modifications and changes as may come within the scope of the following claims:

What is claimed is:

1. An endoscope having an insertion tube with a bending section at its distal end, said insertion tube further including
    a viewing head contained at the distal end of the insertion tube in front of the bending section,
    a stop plate positioned between the viewing head and the bending section,
    at least one control cable having a distal end that passes through both the bending section and the stop plate, and
    terminating means mounted on the distal end of the cable adjacent the stop plate, the terminating means including a helically wound spring that is mounted entirely upon the distal end of the cable and is crimped inwardly along its entire axial length to form a first mechanical joint against the cable and open spaces between adjacent turns of the spring, and a flowable bonding material filling the spaces between the cable and the spring to form a fused bond second joint between the spring and the cable.

2. The endoscope of claim 1 that further includes an end plate having a central hole therein that is mounted on said cable between said spring and said stop plate, and said end plate being crimped into contact with said cable and being joined to said spring and said cable by said bonding material.

3. The endoscope of claim 1 wherein said spring is formed of a strand of wound stainless steel.

4. The endoscope of claim 1 wherein the distal end of the spring and the wire are trimmed to form a substantially flat end face.

5. The endoscope of claim 4 wherein the substantially flat end face is covered with said bonding material.

6. The endoscope of claim 1 that further includes a plurality of cables that pass through the bending section and the stop plate.

7. The endoscope of claim 1 wherein said bonding material is solder.

8. The endoscope of claim 1 wherein said cable is formed of wrapped wire strands and the bonding material fills the spaces between the wire strands to further enhance the joint between the cable and the spring.

9. The endoscope of claim 1 wherein the spring is crimped into a triangular cross sectional configuration.

* * * * *